US 12,179,039 B2
(12) United States Patent
Arai

(10) Patent No.: US 12,179,039 B2
(45) Date of Patent: Dec. 31, 2024

(54) RADIOTHERAPY DEVICE AND MULTI-LEAF COLLIMATOR

(71) Applicant: Hitachi High-Tech Corporation, Tokyo (JP)

(72) Inventor: Satoshi Arai, Hiroshima (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 219 days.

(21) Appl. No.: 17/909,806

(22) PCT Filed: Feb. 2, 2021

(86) PCT No.: PCT/JP2021/003770
§ 371 (c)(1),
(2) Date: Sep. 7, 2022

(87) PCT Pub. No.: WO2021/199656
PCT Pub. Date: Oct. 7, 2021

(65) Prior Publication Data
US 2023/0330434 A1    Oct. 19, 2023

(30) Foreign Application Priority Data
Mar. 31, 2020  (JP) .................... 2020-064346

(51) Int. Cl.
*A61N 5/10* (2006.01)
(52) U.S. Cl.
CPC ......... *A61N 5/1045* (2013.01); *A61N 5/1048* (2013.01)

(58) Field of Classification Search
CPC ............... A61N 5/1045; A61N 5/1048; A61N 2005/1059; G21K 1/046; A61B 90/90; A61B 2090/3941
See application file for complete search history.

(56) References Cited

U.S. PATENT DOCUMENTS

| 10,518,110 B1 | 12/2019 | Jimenez-Carvajal et al. |
| 2009/0196401 A1* | 8/2009 | Awan ............... G21K 1/046 378/150 |
| 2014/0341351 A1 | 11/2014 | Berwick et al. |

(Continued)

FOREIGN PATENT DOCUMENTS

| JP | 5143761 B2 | 2/2013 |
| WO | 2015/107651 A1 | 7/2015 |

(Continued)

OTHER PUBLICATIONS

Extended European Search Report received in corresponding European Application No. 21780903.7 dated Mar. 12, 2024.

(Continued)

*Primary Examiner* — Christine S. Kim
(74) *Attorney, Agent, or Firm* — MATTINGLY & MALUR, PC

(57) ABSTRACT

By using a marker excellent in durability in a multi-leaf collimator, positions of the markers are accurately detected, and positions of the leaves are accurately controlled. The markers are plates containing a phosphor, and surfaces of the plates are fixed to surfaces of the leaves such that end surfaces of the plates are located on predetermined end surfaces of the leaves. An image of the end surfaces of the plates is captured by a camera, and positions of the end surfaces are recognized by image processing.

13 Claims, 15 Drawing Sheets

(56) References Cited

U.S. PATENT DOCUMENTS

2016/0325117 A1* 11/2016 Arai .................. G21K 1/046
2016/0325118 A1   11/2016 Arai
2017/0043185 A1    2/2017 Awan et al.
2018/0021596 A1    1/2018 Arai et al.

FOREIGN PATENT DOCUMENTS

WO    2015/107660 A1   7/2015
WO    2016/121051 A1   8/2016

OTHER PUBLICATIONS

International Search Report of PCT/JP2021/003770 dated Apr. 13, 2021.

* cited by examiner

[FIG. 1]
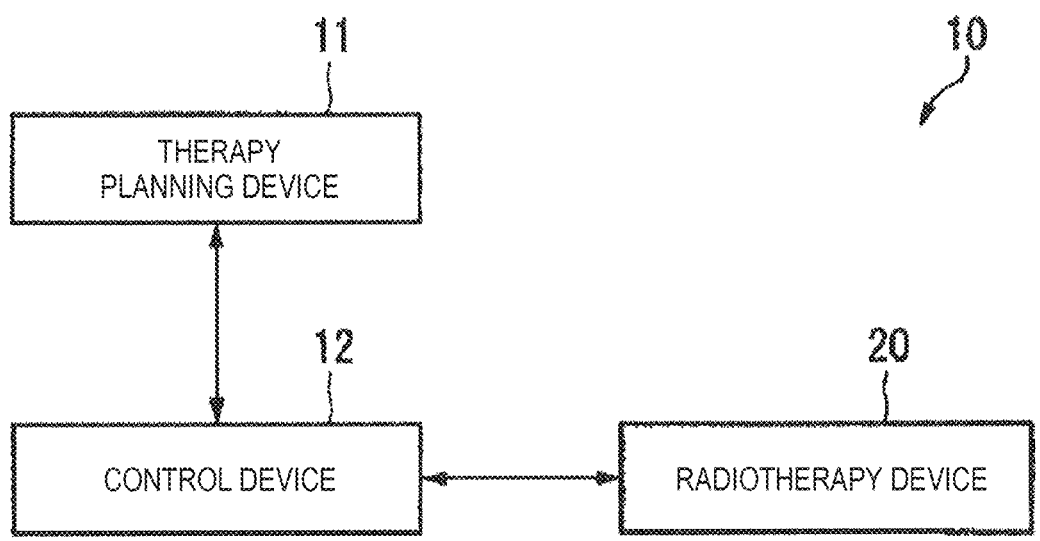

[FIG. 2]
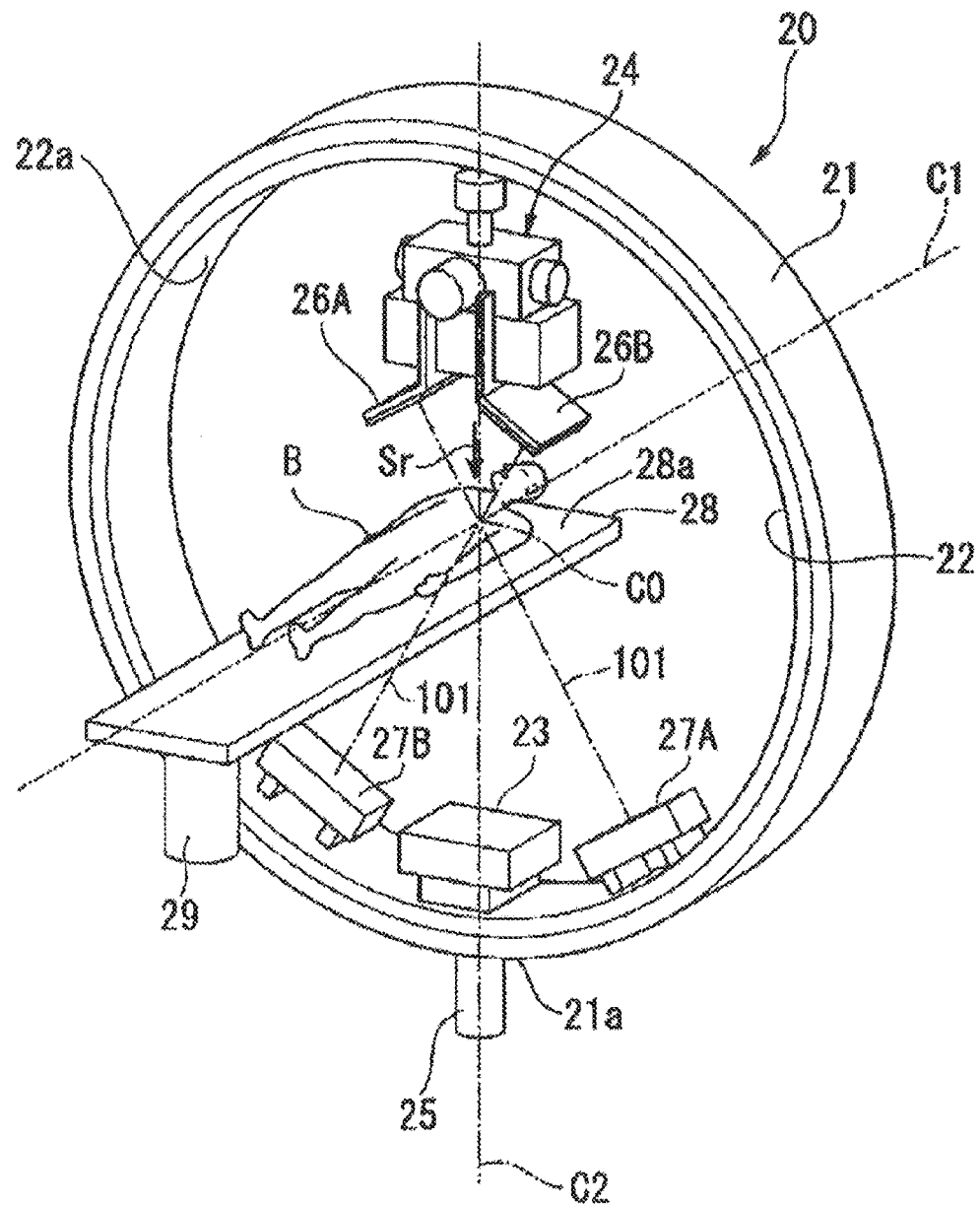

[FIG. 3]
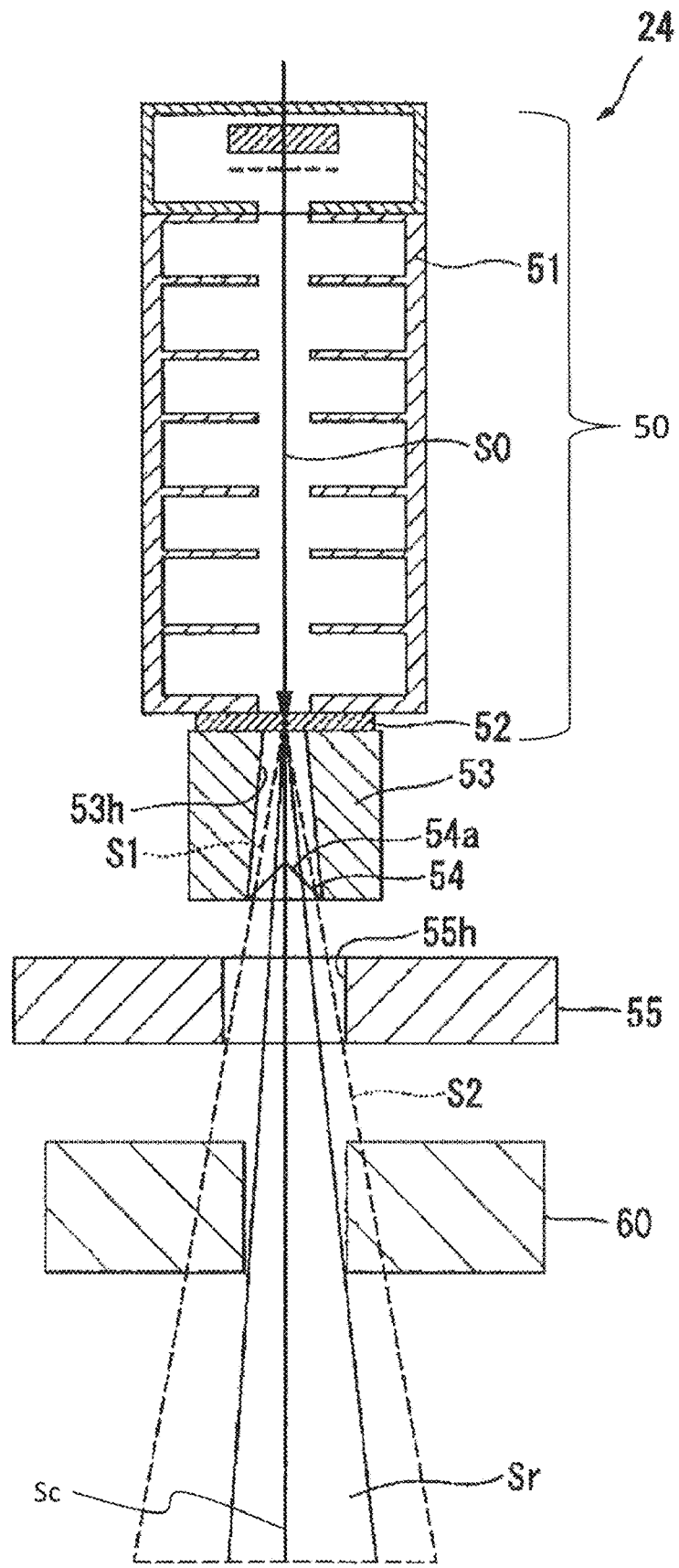

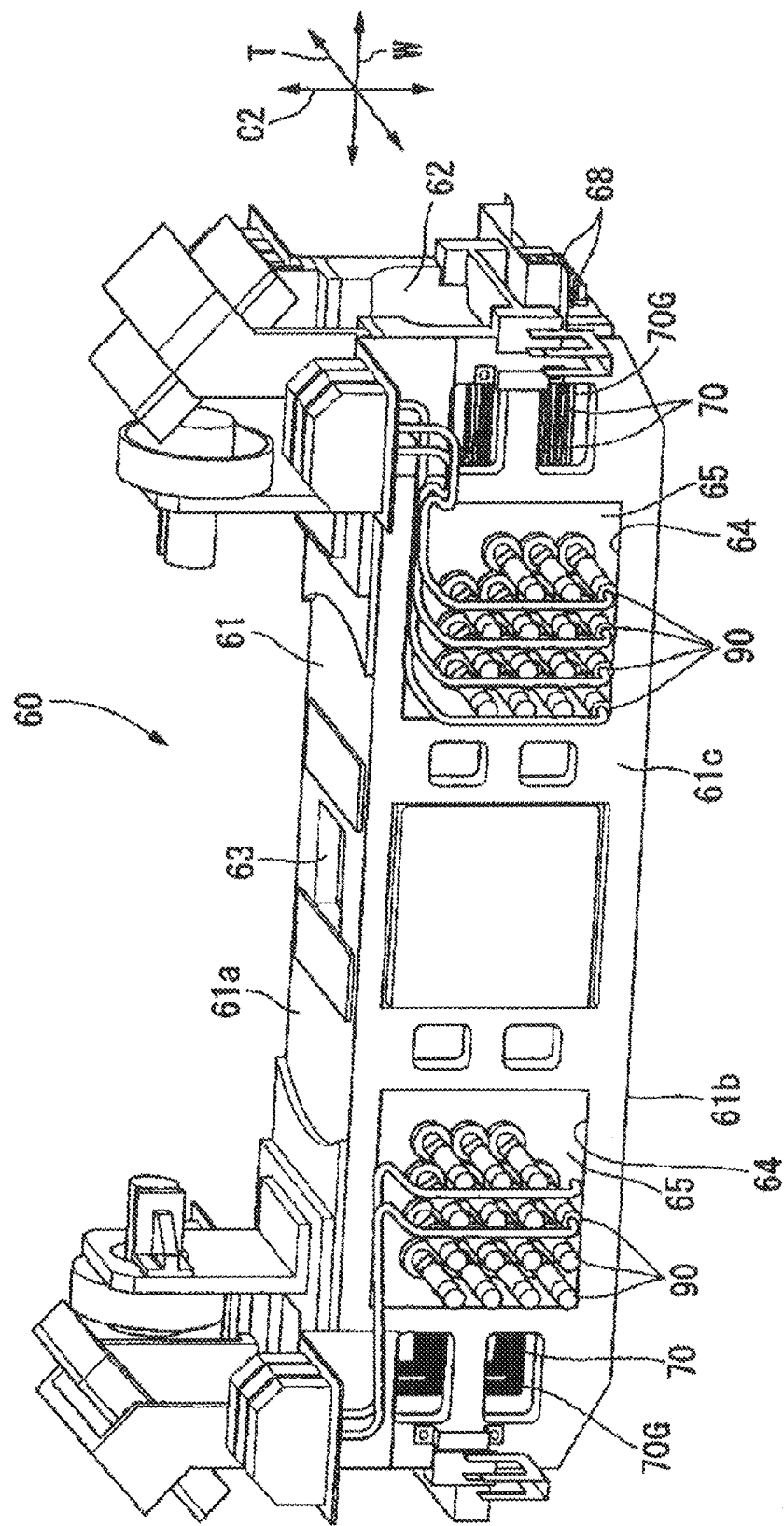
[FIG. 41]

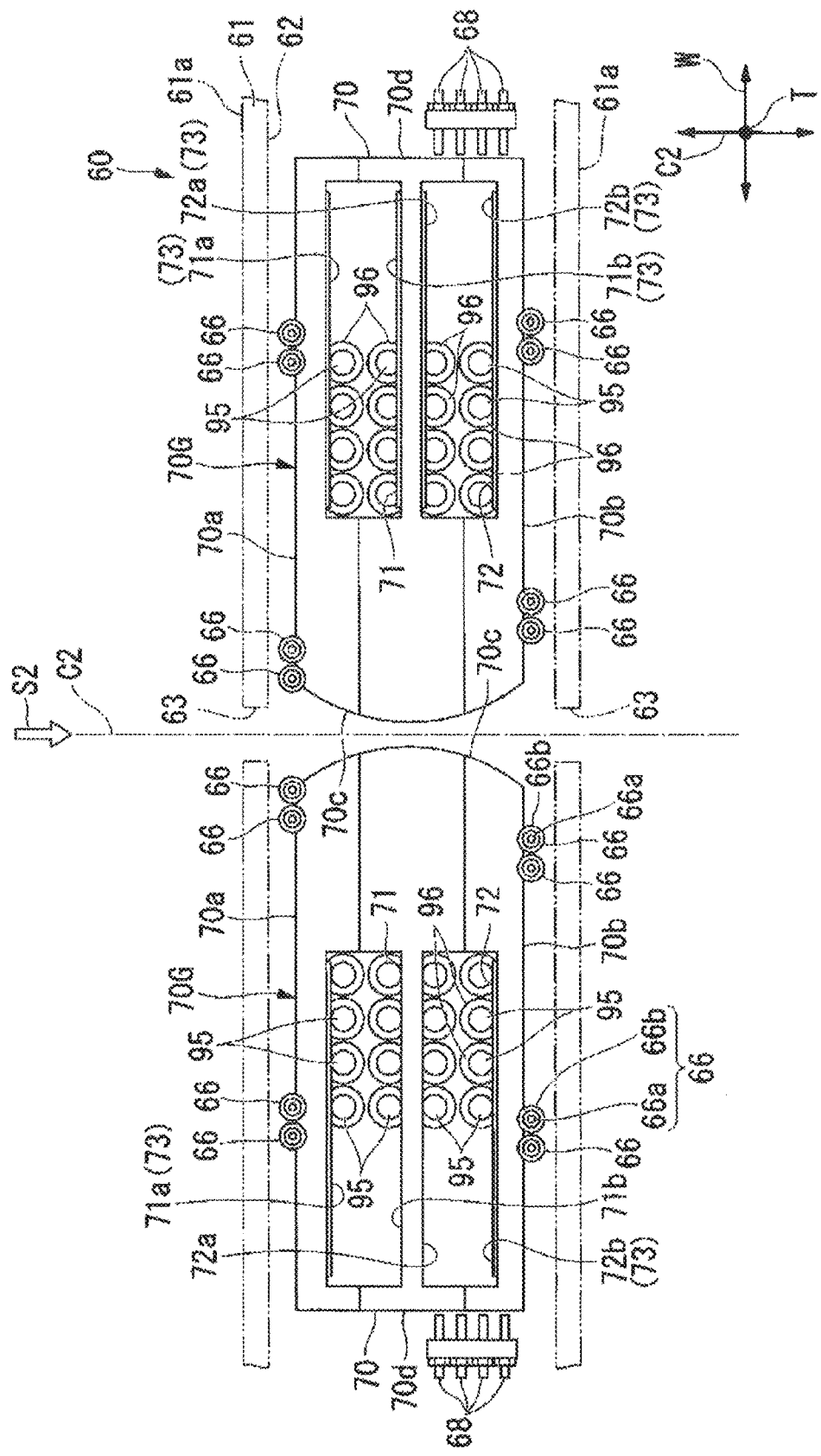
[FIG. 5]

[FIG. 6]
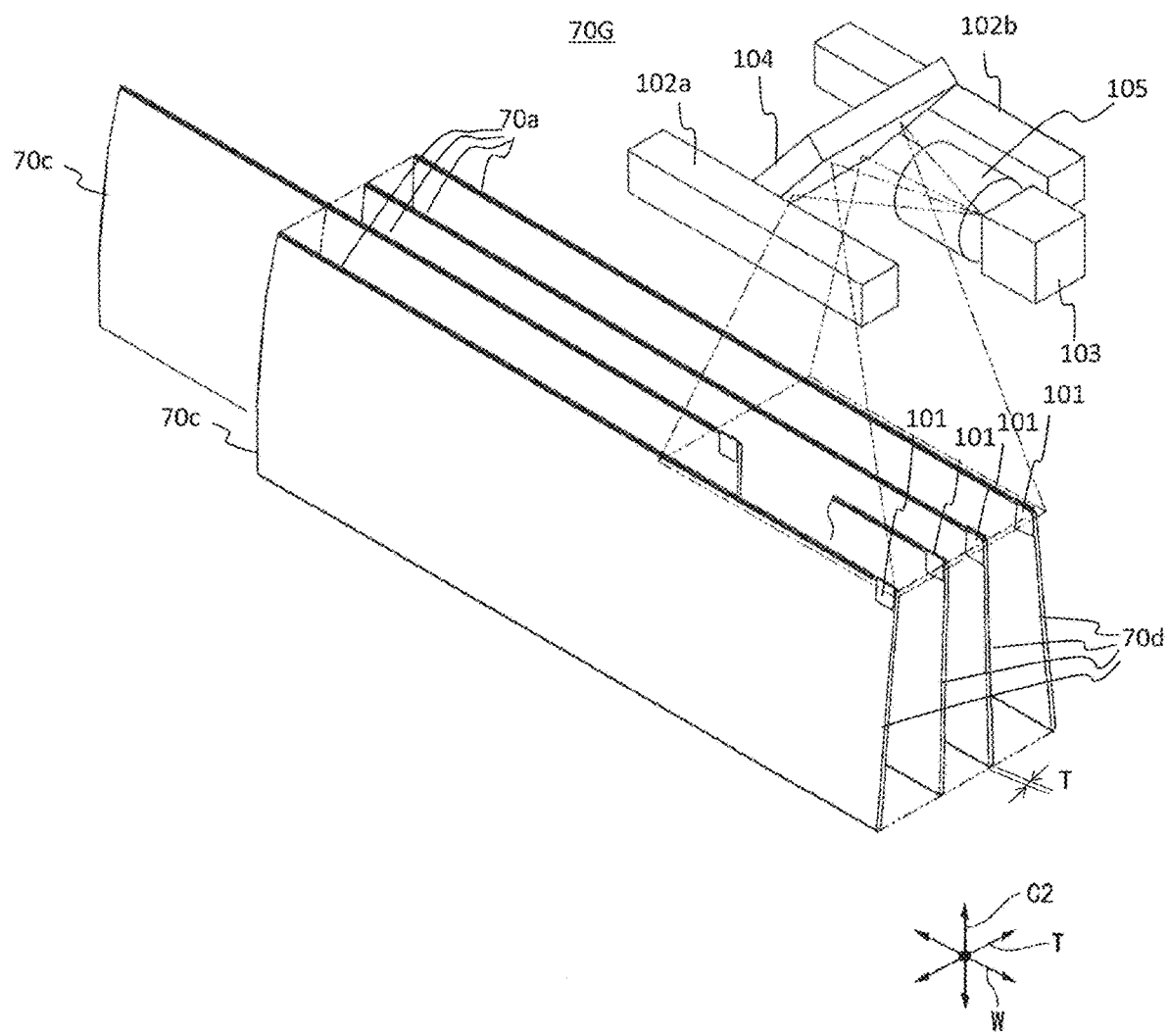

[FIG. 7]
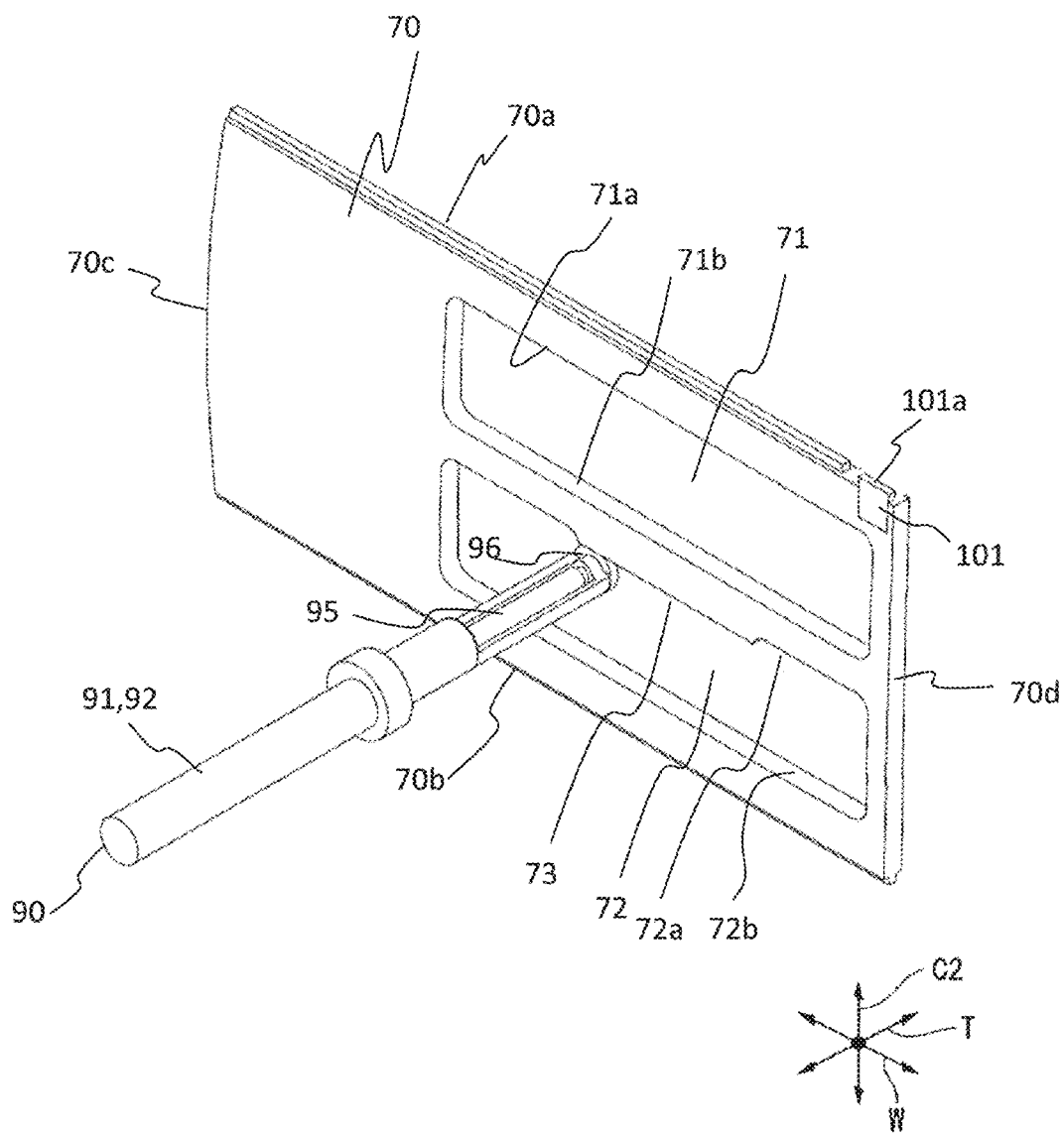

[FIG. 8]
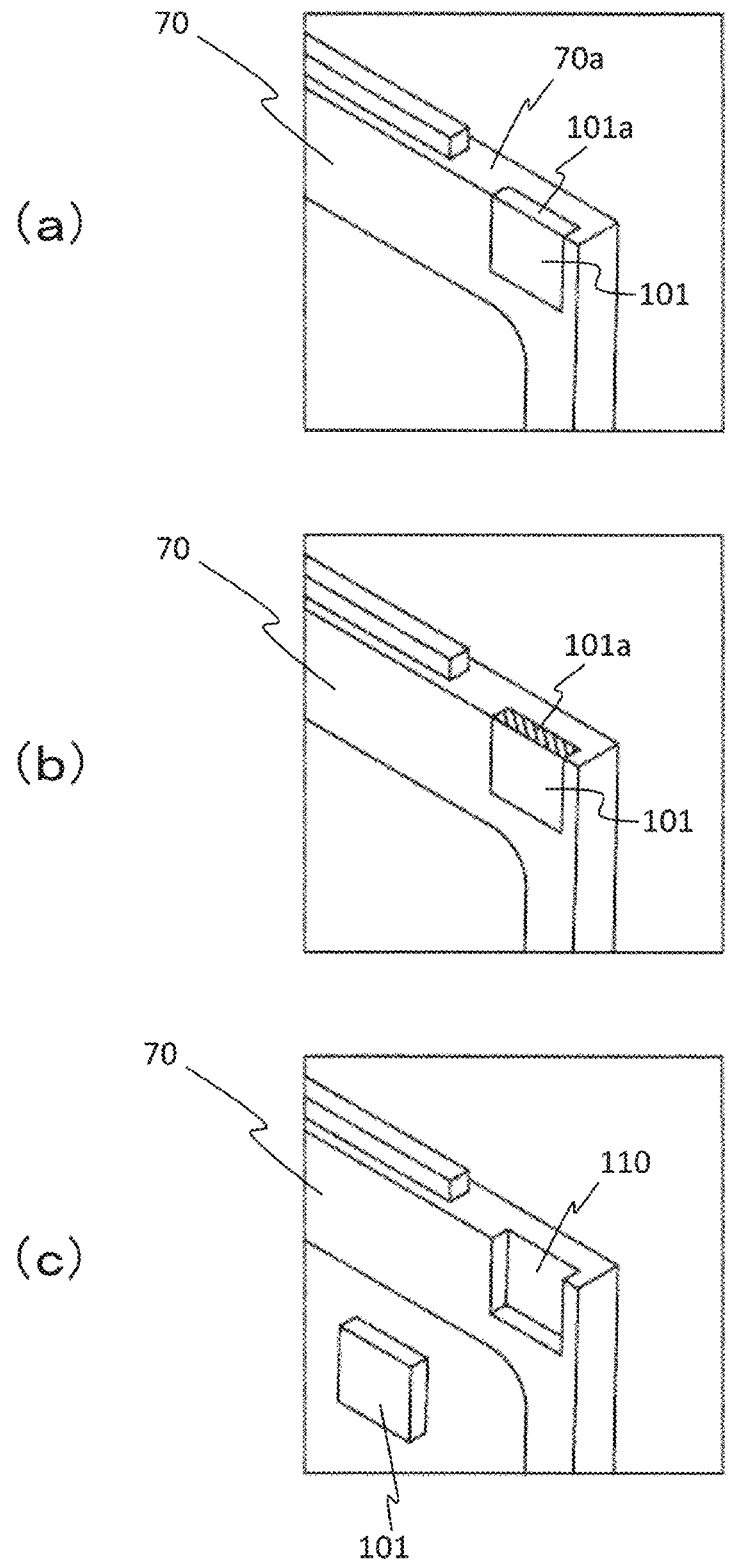

[FIG. 9]
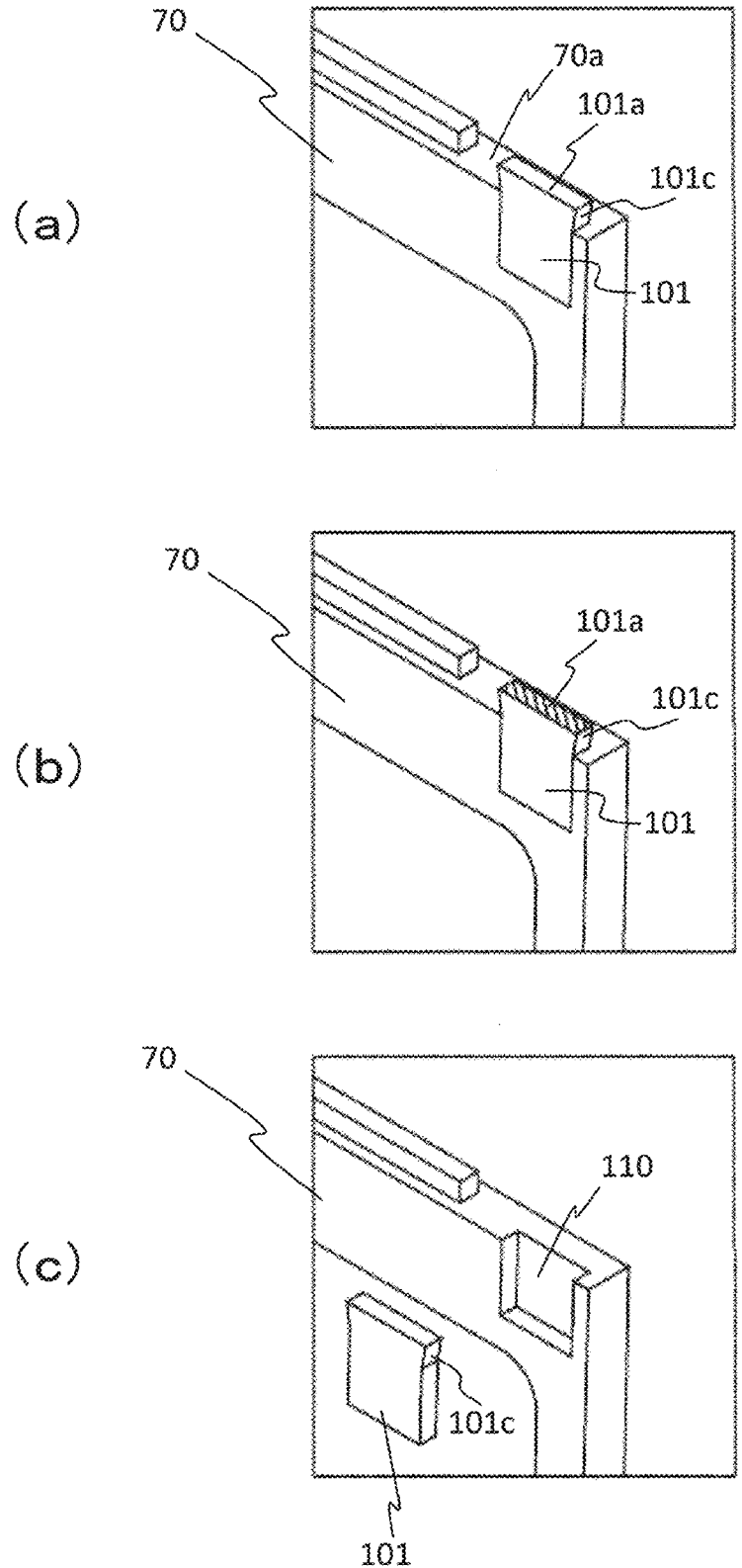

[FIG. 10]
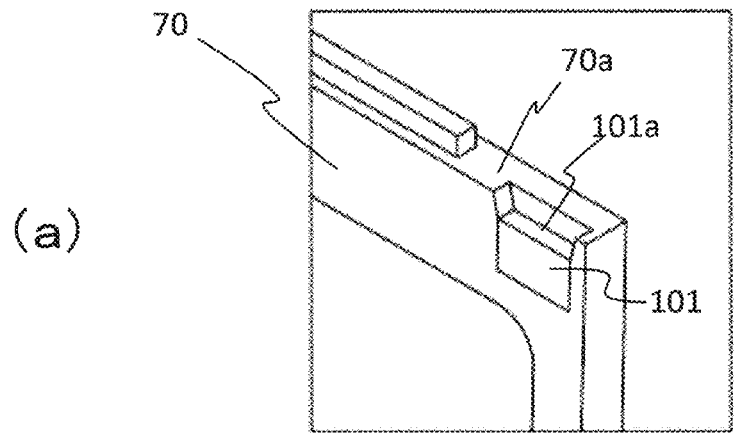
(a)
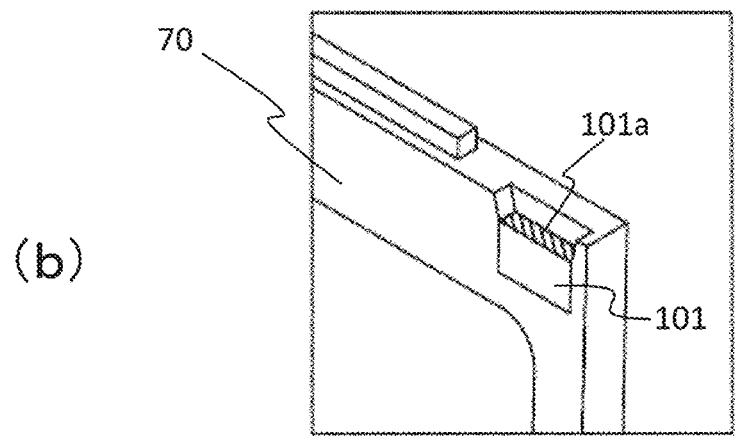
(b)
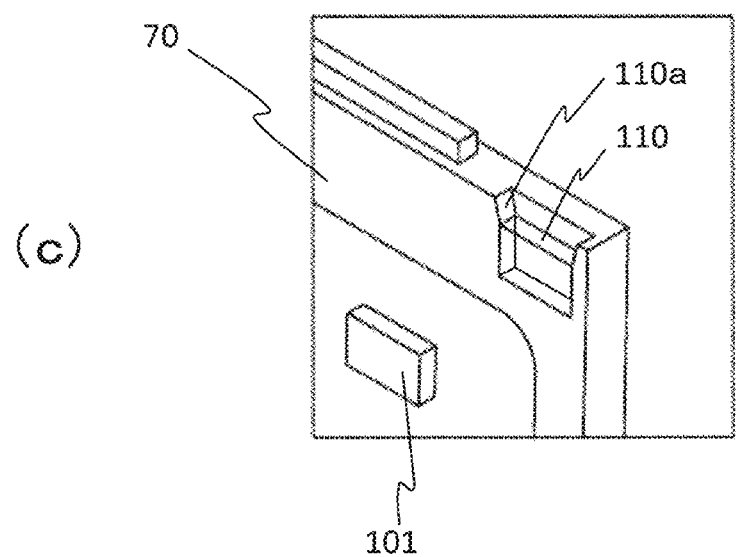
(c)

[FIG. 11]
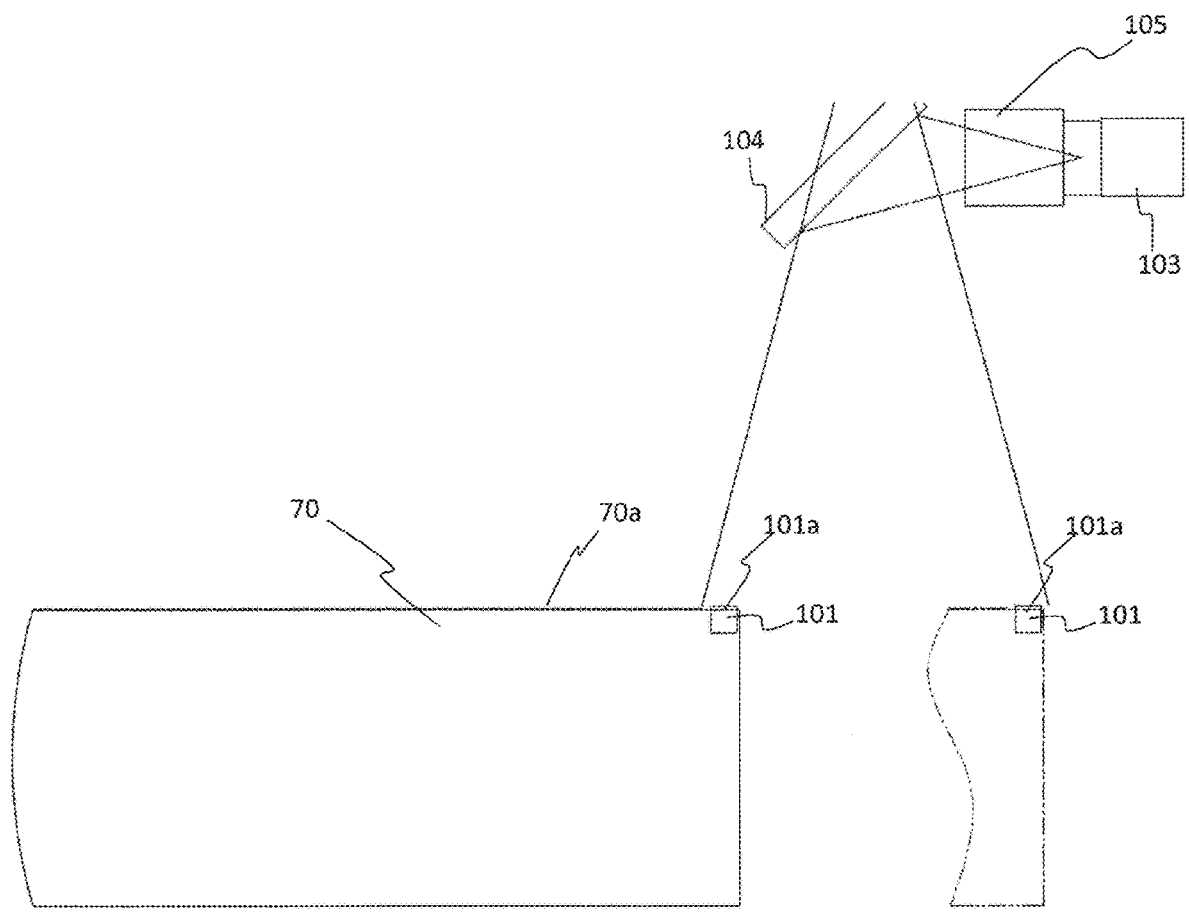

[FIG. 12]
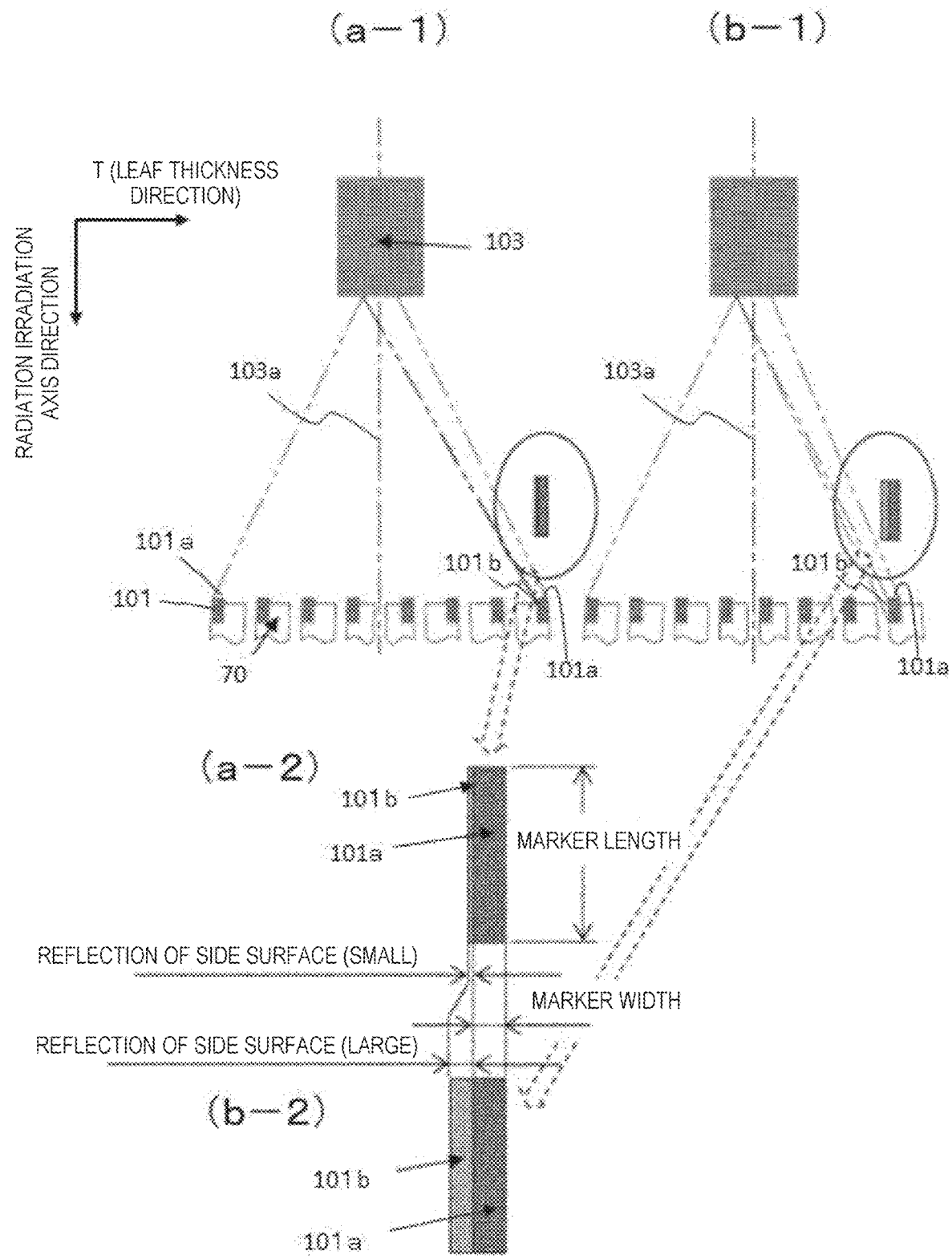

[FIG. 13]
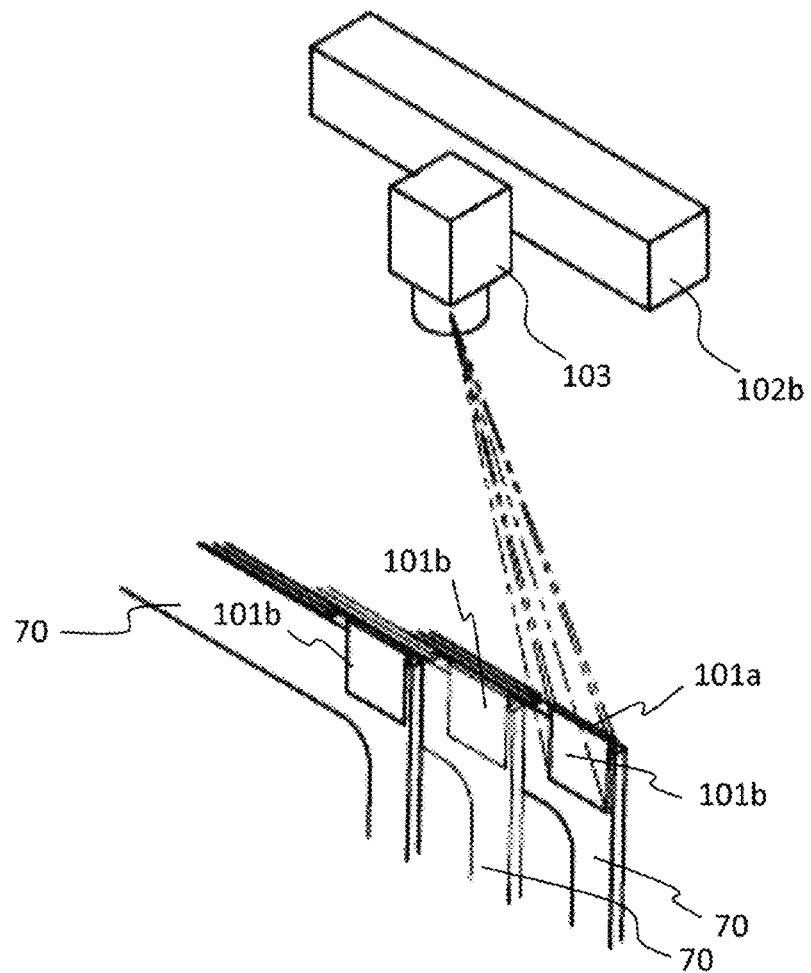

[FIG. 14]
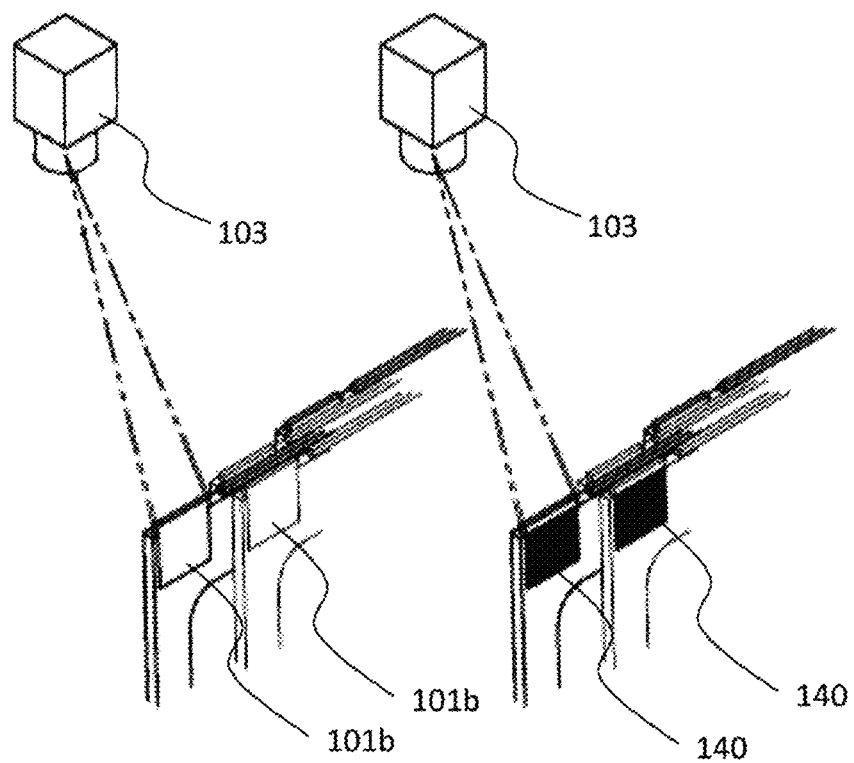

[FIG. 15]
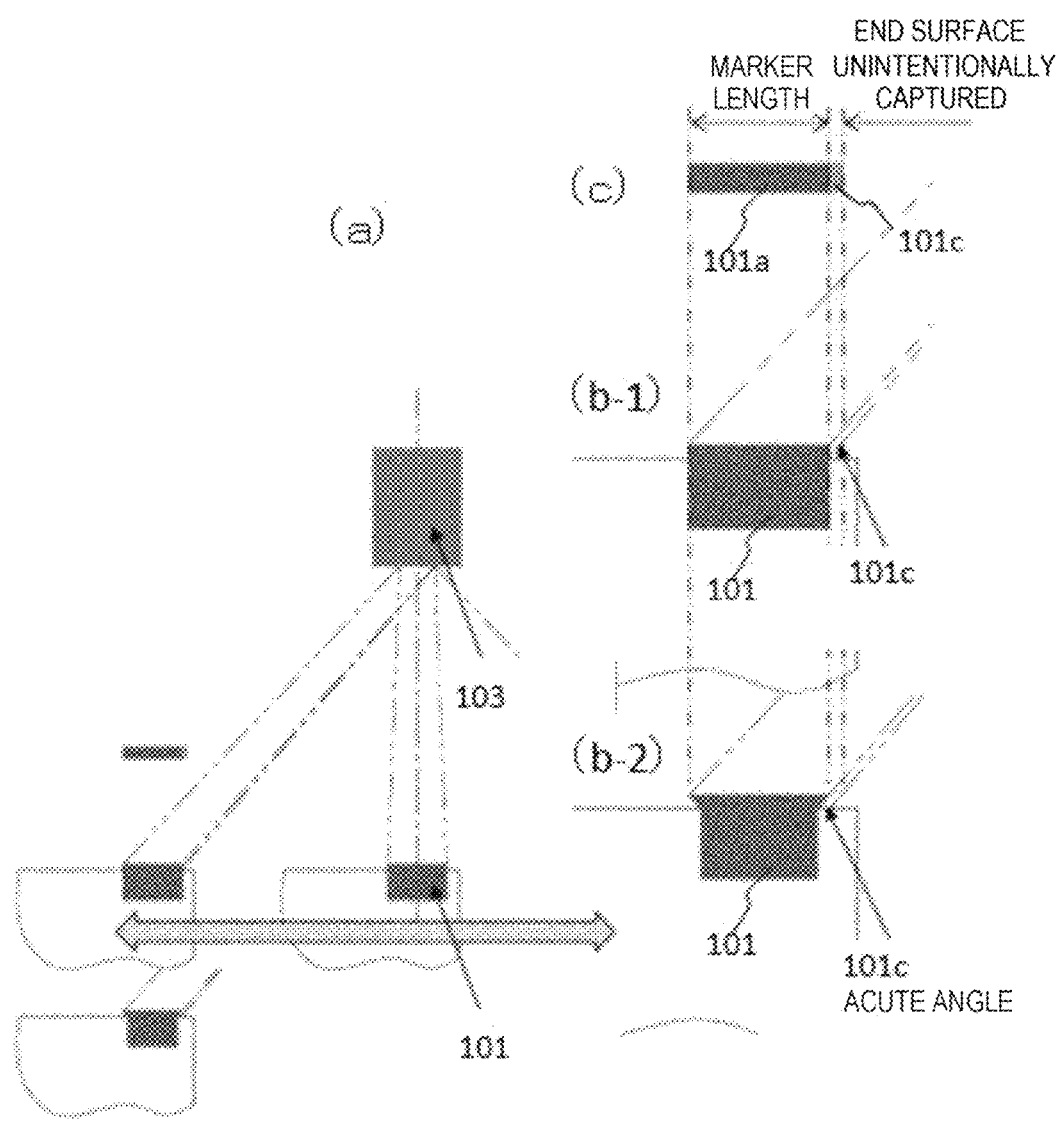

RADIOTHERAPY DEVICE AND MULTI-LEAF COLLIMATOR

TECHNICAL FIELD

The present invention relates to a radiotherapy device, and more particularly, to a radiotherapy device including a multi-leaf collimator that limits an irradiation range of radiation to a desired shape.

BACKGROUND ART

Radiotherapy devices that irradiate tumors or the like with radiation are used in clinical practice. A radiotherapy device includes a multi-leaf collimator in order to reduce as much as possible a dose of radiation with which normal tissues around a tumor are irradiated.

As disclosed in PTLs 1 to 4, a multi-leaf collimator has a structure in which two groups of stacked bodies are disposed to face each other across an optical axis of radiation. In each stacked body, thin plates made of a material that does not allow the radiation to pass therethrough are arranged in a thickness direction at minute intervals. A direction of a main plane of the thin plate is parallel to the optical axis of the radiation. By moving positions of end surfaces of the thin plates one by one according to a contour of a tumor or a shape of a region to be irradiated with the radiation, an opening having a shape surrounding the tumor can be formed by the two groups of thin plate stacked bodies. This makes it possible to irradiate only the tumor with the radiation.

In order to accurately provide the end surfaces of the thin plate stacked bodies of the multi-leaf collimator at positions corresponding to the contour of the tumor, a marker is disposed on an end surface of each thin plate on an outer side. A position of the marker is detected by capturing an image of the marker with a camera or the like, and the position is used for comparison and determination with a feedback control result of movement of the thin plate.

In a device according to PTL 1, ruby is used as the marker, while in devices according to PTLs 2 and 3, paint or the like containing a phosphor is applied as the marker. These markers are irradiated with excitation light, and an image of fluorescence emitted from each of the markers is captured by the camera.

CITATION LIST

Patent Literature

PTL 1: Japanese Patent No. 5143761
PTL 2: WO 2015/107651
PTL 3: WO 2015/107660
PTL 4: WO 2016/121051

SUMMARY OF INVENTION

Technical Problem

As an example of a method for controlling a thin plate based on a position of a marker in the multi-leaf collimator, a method is used in which a length and a width of the marker are detected by processing an image of the marker captured by the camera, and movement of the thin plate is feedback-controlled such that the position of the marker of the thin plate is located at a desired position, for example, using a center position of the marker as the position of the marker. Therefore, it is important that the length and width of the marker are predetermined sizes.

In a configuration in which the ruby is used as the marker as in PTL 1, the ruby has high hardness and is not easily processed, and thus a manufacturing cost increases.

PTLs 2 and 3 disclose that the marker is formed by applying a fluorescent pigment or a fluorescent paint.

However, when the marker is formed by applying the fluorescent pigment or the fluorescent paint, the marker may be peeled off from the end surface of the thin plate because the marker is a coating film. When a part of the marker is peeled off from the end surface of the thin plate, the length of the marker changes. When a position of the thin plate is detected based on a center of the length of the marker, erroneous position detection is performed.

In particular, in recent years, thin plates (hereinafter referred to as leaves) of a multi-leaf collimator has been reduced in thickness, and a thickness of the leaves has been reduced to 1 mm or smaller. Markers disposed on end surfaces of the leaves need to be formed such that a width of the markers in a thickness direction of the leaves are approximately half the thickness of the leaves in order to recognize markers of adjacent leaves as separate markers by image processing. Therefore, when the thickness of the leaves is 1 mm or smaller, the width of the markers is 0.5 mm or smaller. It is not easy to apply the fluorescent paint to regions having a width of 0.5 mm or smaller. Since the formed markers have a minute contact area with the end surfaces of the leaves, it is difficult to improve adhesion between the markers and the end surfaces of the leaves, and peeling is likely to occur.

Since a plurality of leaves are arranged in the thickness direction with gaps smaller than the thickness of the leaves, the width of the markers cannot be made larger than the thickness of the leaves in order to avoid collision between a marker and a leaf adjacent to the marker.

In order to accurately recognize the length and width of the markers by processing an image captured by a camera, an amount of light emitted from the markers need to be a predetermined amount or more, and the markers need to be formed using a material containing a necessary amount or more of a phosphor.

An object of the present invention is to accurately detect positions of markers and accurately control positions of leaves by using the markers that are less likely to peel off from end surfaces in a multi-leaf collimator.

Solution to Problem

In order to achieve the above object, a radiotherapy device according to the invention includes a radiation source; and a multi-leaf collimator configured to limit an irradiation range of radiation radiated from the radiation source. The multi-leaf collimator includes: a plurality of thin plate-shaped leaves made of a material that does not allow the radiation to pass therethrough, the plurality of thin plate-shaped leaves being arranged in a thickness direction; markers containing a phosphor, the markers being disposed on predetermined end surfaces of the leaves; a light source configured to irradiate the markers with light that excites the phosphor; and a camera configured to capture an image of fluorescence emitted from the markers, the camera being disposed at a position where the camera faces the predetermined end surfaces of the leaves. The markers are plates containing the phosphor, and surfaces of the plates are fixed to surfaces of the leaves such that end surfaces of the plates are located on the predetermined end surfaces of the leaves. An image of the end surfaces of the plates is captured by the camera.

Advantageous Effects of Invention

According to the present invention, since the plates containing the phosphor are inserted in the plurality of leaves and fixed to one of the leaves, and the end surfaces are used as the markers, the markers are less likely to peel off, positions of the markers can be accurately detected by capturing an image of the markers with the camera, and positions of the leaves can be accurately controlled.

BRIEF DESCRIPTION OF DRAWINGS

FIG. 1 is a block diagram of a radiotherapy system 10 according to an embodiment of the invention.

FIG. 2 is a perspective view of a radiotherapy device 20 according to the embodiment.

FIG. 3 is a cross-sectional view showing a schematic configuration of a radiation irradiation device 24 in the radiotherapy device 20 in FIG. 2.

FIG. 4 is a perspective view of a multi-leaf collimator of the radiation irradiation device 24 in FIG. 3.

FIG. 5 is a cross-sectional view of the multi-leaf collimator in FIG. 4.

FIG. 6 is a perspective view showing a configuration example of a leaf group 70G of the multi-leaf collimator in FIG. 4.

FIG. 7 is a perspective view of a leaf 70 and a driving device 90 of the multi-leaf collimator in FIG. 4.

FIG. 8 (a) of FIG. 8 is an enlarged perspective view of a plate 101 portion of the leaf 70 in FIG. 7, (b) of FIG. 8 is an explanatory view showing an upper end surface 101a recognized as a marker, and (c) of FIG. 8 is an enlarged perspective view showing a recess 110 for fixing the plate 101 to the leaf 70, and the plate 110.

FIG. 9 (a) of FIG. 9 is an enlarged perspective view of the plate 101 portion of the leaf 70 in FIG. 7, (b) of FIG. 9 is an explanatory view showing the upper end surface 101a recognized as a marker, and (c) of FIG. 9 is an enlarged perspective view showing the recess 110 for fixing the plate 101 to the leaf 70, and the plate 110.

FIG. 10 (a) of FIG. 10 is an enlarged perspective view of the plate 101 portion of the leaf 70 in FIG. 7, (b) of FIG. 10 is an explanatory view showing the upper end surface 101a recognized as a marker, and (c) of FIG. 10 is an enlarged perspective view showing the recess 110 for fixing the plate 101 to the leaf 70, and the plate 110.

FIG. 11 is an explanatory view showing an image of a range of a position of the plate 101 captured by a camera 103 according to the embodiment.

FIG. 12 (a-1) and (a-2) of FIG. 12 are an explanatory view showing an example in which the plates 101 are disposed on surfaces of the leaves 70 on an outer side with respect to an optical axis 103a according to the embodiment and an explanatory view showing an image example of the camera 103 at that time, and (b-1) and (b-2) of FIG. 12 are an explanatory view showing an example in which the plates 101 are disposed on surfaces of the leaves 70 on the same side according to the embodiment and an explanatory view showing an image example of the camera 103 at that time.

FIG. 13 is a perspective view showing that an image of surfaces 101b of the plates 101 is captured by the camera 103 in arrangement in (b-1) of FIG. 12.

FIG. 14 (a) of FIG. 14 is a perspective view showing a state in which the surfaces 101b of the plates 101 are exposed in arrangement in (a-1) of FIG. 12, and (b) of FIG. 14 is a perspective view showing a state in which light shielding members 140 are disposed on the surfaces 101b of the plates 101.

FIGS. 15 (a), (b-1), and (c) of FIG. 15 are explanatory views that a side surface 101c is unintentionally captured by the camera when the upper end surface 101a of the plate 101 according to the embodiment is disposed so as to protrude from a predetermined upper end surface 70a of the leaf 70 by a predetermined amount, and (b-2) of FIG. 15 is an explanatory view showing a shape in which the side surface 101c of the plate 101 according to the embodiment is formed at an acute angle with respect to the upper end surface.

DESCRIPTION OF EMBODIMENTS

A radiotherapy system according to an embodiment of the invention will be described.

<Overview of Radiotherapy Device>

First, an overall configuration of the radiotherapy system according to the present embodiment will be described.

FIG. 1 is a diagram showing a functional configuration of a radiotherapy system 10 according to the embodiment of the invention.

As shown in FIG. 1, the radiotherapy system 10 includes a therapy planning device 11, a control device (control unit) 12, and a radiotherapy device 20.

The therapy planning device 11 is a device that receives, from the outside, properties of radiation to be radiated to a patient B (intensity, time, angle, position, radiation region, and the like of radiation radiated to the patient B), which is set in advance according to a content of radiotherapy to be performed on the patient B. The therapy planning device 11 outputs, to the control device 12, various control parameter values for radiating radiation corresponding to the received properties of the radiation.

The control device 12 controls an operation of the radiotherapy device 20 based on the various parameter values generated by the therapy planning device 11. The control device 12 is a computer device such as a personal computer that executes processing based on a predetermined program. The control device 12 is connected to the radiotherapy device 20 wirelessly or via a wired communication line such that information can be transmitted bidirectionally.

FIG. 2 is a perspective view showing a schematic configuration of the radiotherapy device 20 constituting the radiotherapy system 10.

As shown in FIG. 2, the radiotherapy device 20 includes a ring frame 21, a moving gantry 22, and a radiation irradiation device 24.

The ring frame 21 is formed in a cylindrical shape having a circular cross section. The ring frame 21 is disposed such that a central axis C1 is oriented substantially in a horizontal direction. A rotation shaft 25 extending downward is integrally formed on an outer peripheral surface of a lower end portion 21a of the ring frame 21. The rotation shaft 25 is supported by a base (not shown) so as to be rotatable about a central axis C2 thereof. The rotation shaft 25 is rotationally driven by a turning driving mechanism (not shown). That is, the ring frame 21 turns around a vertical axis as the rotation shaft 25 is rotated by the turning driving mechanism.

The moving gantry 22 is formed in a cylindrical shape having a circular cross section. The moving gantry 22 is disposed on an inner circumferential side of the ring frame 21. The moving gantry 22 is supported by the ring frame 21 and is rotatable along an inner circumferential surface of the ring frame 21. In other words, the annular moving gantry 22 is rotatable about the central axis C1 extending in the horizontal direction. The moving gantry 22 is rotated in a circumferential direction by a gantry driving mechanism (not shown).

The radiation irradiation device 24 is controlled by the control device 12 (see FIG. 1) to radiate therapeutic radiation Sr. The radiation irradiation device 24 is supported by an inner circumferential surface 22a of the moving gantry 22. The therapeutic radiation Sr radiated from the radiation irradiation device 24 is adjusted so as to pass through an isocenter C0, which is an intersection of the central axis C2 of a rotation operation of the ring frame 21 and the central axis C1 of a rotation operation of the moving gantry 22.

Since the radiation irradiation device 24 is supported by the moving gantry 22 in this way, the therapeutic radiation Sr is radiated so as to always pass through the isocenter C0 regardless of the rotation operation of the ring frame 21 about the central axis C2 and the rotation operation of the moving gantry 22 about the central axis C1.

The radiotherapy device 20 further includes a sensor array 23. The sensor array 23 receives the therapeutic radiation Sr radiated by the radiation irradiation device 24 and transmitted through a subject around the isocenter C0, and generates a transmission image of the subject. A flat panel detector (FPD), an X-ray image intensifier (II), or the like can be used as the sensor array 23.

The radiotherapy device 20 includes diagnostic X-ray sources 26A, 26B and sensor arrays 27A, 27B.

The diagnostic X-ray sources 26A, 26B are disposed on an inner circumferential side of the moving gantry 22. The diagnostic X-ray sources 26A, 26B are disposed on both sides of the ring frame 21 in the circumferential direction across a center of the radiotherapy device 20 (in other words, the central axis C2 of the rotation operation of the ring frame 21). The diagnostic X-ray sources 26A, 26B are controlled by the control device 12 to radiate diagnostic X-rays 101 toward the isocenter C0. The diagnostic X-rays 101 form a conical beam that spreads in a conical shape from one point of each of the diagnostic X-ray sources 26A, 26B.

The sensor arrays 27A, 27B are supported by the inner circumferential surface 22a of the moving gantry 22. The sensor arrays 27A, 27B are disposed so as to face the diagnostic X-ray sources 26A, 26B across the isocenter C0. The sensor arrays 27A, 27B receive the diagnostic X-rays 101 radiated from the diagnostic X-ray sources 26A, 26B, respectively and transmitted through the subject around the isocenter C0, and generate the transmission image of the subject. For example, a flat panel detector (FPD), an X-ray image intensifier (II), or the like can be used as each of the sensor arrays 27A, 27B.

The radiotherapy device 20 further includes a couch 28 and a couch driving device 29. The couch 28 includes an upper surface 28a on which the patient B to be treated by the radiotherapy system 10 lies horizontally.

The couch driving device 29 is controlled by the control device 12 to move the couch 28. The couch driving device 29 is supported by a base (not shown).

<Configuration of Radiation Irradiation Device>

FIG. 3 is a cross-sectional view showing the radiation irradiation device 24 constituting the radiotherapy device 20.

As shown in FIG. 3, the radiation irradiation device 24 includes a radiation source 50, a primary collimator 53, a flattening filter 54, a secondary collimator 55, and a multi-leaf collimator 60. Here, the radiation source 50 is an X-ray source including an electron beam accelerator 51 and an X-ray target 52.

The electron beam accelerator 51 irradiates the X-ray target 52 with an electron beam S0 generated by accelerating electrons.

The X-ray target 52 is made of tungsten, a tungsten alloy, or the like. The X-ray target 52 radiates radiation S1 when irradiated with the electron beam S0.

The primary collimator 53 shields a part of the radiation S1 such that the radiation S1 is not radiated to a portion other than a desired portion. The primary collimator 53 includes a through hole 53h through which the radiation S1 radiated from the X-ray target 52 passes. The primary collimator 53 is made of lead, tungsten, or the like.

The flattening filter 54 is a filter that distributes a dose of the radiation S1 substantially uniformly in a plane perpendicular to a radiation direction of the radiation S1. The flattening filter 54 is made of aluminum or the like. The flattening filter 54 is disposed on an outlet side of the through hole 53h of the primary collimator 53. The flattening filter 54 has a substantially conical protrusion 54a on a side facing the X-ray target 52. A shape of the protrusion 54a is designed such that the dose of the radiation S1 is substantially uniformly distributed in the plane perpendicular to the radiation direction of the radiation S1.

The secondary collimator 55 shields a part of the radiation S1. The secondary collimator 55 has a through hole 55h at a central portion thereof. The secondary collimator 55 allows radiation S2 to pass through only the through hole 55h. The secondary collimator 55 is made of lead, tungsten, or the like.

By passing through the primary collimator 53, the flattening filter 54, and the secondary collimator 55 described above, a part of the radiation S2 having a uniform intensity distribution is further shielded by the multi-leaf collimator 60. The multi-leaf collimator 60 is controlled by the control device 12 to limit an irradiation field of the radiation S2. The multi-leaf collimator 60 generates therapeutic radiation Sr according to the properties of the radiation to be radiated to the patient.

<Overall Configuration of Multi-Leaf Collimator>

Hereinafter, a configuration of the multi-leaf collimator will be described in more detail.

FIG. 4 is a perspective view showing an appearance of the multi-leaf collimator 60 constituting a part of the radiation irradiation device 24. FIG. 5 is a cross-sectional view in a width direction of the multi-leaf collimator 60. FIG. 6 is a perspective view showing an outline of a leaf group 70G, in which a plurality of leaves 70 are arranged, of the multi-leaf collimator 60. FIG. 7 is a perspective view of one leaf 70.

As shown in FIGS. 4 to 7, the multi-leaf collimator 60 includes a frame 61, the plurality of leaves 70, and driving devices (driving mechanisms) 90.

The frame 61 is formed in a rectangular parallelepiped shape elongated in one direction. The frame 61 is disposed such that a first direction (hereinafter referred to as a width direction W), which is a longitudinal direction of the frame 61, is orthogonal to a radiation irradiation axis Sc of the radiation irradiation device 24. The frame 61 is provided with a hollow leaf accommodating portion 62 that is continuous in the width direction W thereof.

The frame 61 is provided with openings 63 penetrating outer peripheral sides of the frame 61 and the leaf accommodating portion 62 in an upper surface portion 61a on a side facing the radiation irradiation device 24 and a lower surface portion 61b on an opposite side (FIG. 4 shows only the opening 63 of the upper surface portion 61a). These openings 63 are formed in central portions of the upper surface portion 61a and the lower surface portion 61b in the width direction W.

As shown in FIGS. 4 and 5, in the frame 61, rectangular openings 64, 64 are formed in both side surface portions 61c, 61d orthogonal to the upper surface portion 61a and the lower surface portion 61b, respectively. The openings 64 in the side surface portion 61c and the openings 64 in the side surface portion 61d are formed to be plane-symmetrical with respect to a virtual plane positioned at a center between the side surface portion 61c and the side surface portion 61d. Rectangular base plates 65 are attached to the openings 64, respectively. In this embodiment, a case where the opening 64 is formed in the frame 61 and the base plate 65 is attached is illustrated. However, the invention is not limited to this configuration. For example, the frame 61 and the base plate 65 may be integrally formed, and the opening 64 may not be formed in the frame 61.

The leaf 70 is formed in a substantially rectangular thin plate shape. The leaf 70 is made of, for example, tungsten, a tungsten alloy, or the like through which the radiation S2 does not pass.

As shown in FIGS. 5 and 6, the leaves 70 are arranged at predetermined intervals in a thickness direction T. The plurality of leaves 70 constitute the leaf group 70G. The leaf group 70G according to this embodiment includes, for example, thirty leaves 70. As shown in FIGS. 4 and 6, two sets of such leaf groups 70G are disposed in the leaf accommodating portion 62 in the frame 61 so as to face each other across the radiation irradiation axis Sc (a central portion of the frame 61 in the width direction W). The number of leaves 70 in the leaf group 70G is not limited to 30, and can be changed according to performance of the therapy machine, for example.

In FIG. 6, for convenience of illustration, an interval between the leaves 70 is shown wider than a thickness T of the leaf 70, but actually, the interval between the leaves 70 is smaller than the thickness T of the leaf 70.

FIG. 7 is a perspective view showing the leaf 70 and a driving device 90 that drives the leaf 70.

As shown in FIG. 7, the leaf 70 is formed such that a linear upper edge portion (end surface) 70a and a linear lower edge portion 70b are parallel to each other. As shown in FIG. 5, in the leaf accommodating portion 62, the upper edge portion 70a is disposed to face the upper surface portion 61a with an interval therebetween. Similarly, in the leaf accommodating portion 62, the lower edge portion 70b is disposed to face the lower surface portion 61b with an interval therebetween.

The leaf 70 is formed such that a front edge portion 70c on a side facing a central portion of the frame 61 in the width direction W in the leaf accommodating portion 62 bulges in an arc shape. In the leaf 70, a rear edge portion 70d facing an outer side of the frame 61 in the width direction W in the leaf accommodating portion 62 is formed in a linear shape orthogonal to the upper edge portion 70a and the lower edge portion 70b.

A pair of two groups, namely the leaf groups 70G, 70G disposed to face each other across the central portion in the width direction W in the leaf accommodating portion 62 are disposed such that the front edge portion 70c of each leaf faces a region (region including the radiation irradiation axis Sc) in a space between the opening 63 in the upper surface portion 61a and the opening 63 in the lower surface portion 61b of the frame 61.

Each leaf 70 includes slits 71, 72 penetrating in the thickness direction T. These slits 71, 72 are formed continuously in a direction in which the front edge portion 70c and the rear edge portion 70d of the leaf 70 are connected, that is, in the width direction W. The slits 71, 72 are formed at an interval in a direction in which the upper edge portion 70a and the lower edge portion 70b of the leaf 70 are connected. These slits 71, 72 are formed at positions shifted to a rear edge portion 70d side from the front edge portion 70c so as not to be irradiated with the radiation S2 incident into the leaf accommodating portion 62 of the frame 61 from the opening 63 of the upper surface portion 61a of the frame 61.

In each leaf 70, a rack gear 73 continuous in the width direction W is formed in at least one of upper side portions 71a, 72a and lower side portions 71b, 72b of the slits 71, 72 (72a in FIG. 7).

The driving device 90 includes a motor 91, a shaft 95, and a pinion gear 96. The motor 91 is connected to a proximal end portion of the shaft 95. The motor 91 rotates the pinion gear 96 by rotationally driving the shaft 95 about an axis thereof.

The driving devices 90 are respectively provided corresponding to the plurality of leaves 70.

As shown in FIG. 7, the shaft 95 of the driving device 90 extends in the plate thickness direction T of the leaf 70. The driving device 90 is inserted into the slit 71 or 72 (72 in FIG. 7), and the pinion gear 96 is disposed so as to mesh with the rack gear 73. Accordingly, the leaf 70 can be moved in the width direction W by the motor 91 rotating the pinion gear 96.

Here, in the leaf group 70G according to this embodiment, the rack gears 73, of the leaves 70, 70 adjacent to each other in a direction in which the plurality of leaves 70 are arranged, are formed on sides different from each other of the upper side portions 71a, 72a and the lower side portions 71b, 72b of the slits 71, 72. With this structure, it is possible to prevent the pinion gear 96 meshing with the rack gear 73 from interfering between the leaves 70, 70 adjacent to each other in the plate thickness direction T.

The plurality of leaves 70 constituting each leaf group 70G are supported by the frame 61. The frame 61 supports the leaves 70 such that the leaves 70 are movable forward and backward in the width direction W perpendicular to the plate thickness direction T. The frame 61 includes a plurality of slide support members 66. The plurality of slide support members 66 are disposed at intervals in the width direction W at an upper portion and a lower portion of each leaf group 70G. In this embodiment, a total of four slide support members 66 that guide movement of the leaves 70 are provided on each of the upper portion and the lower portion of each leaf group 70G, two on a central portion side and two on an outer peripheral side of the frame 61 in the width direction W.

As shown in FIG. 5, each slide support member 66 includes a shaft 66a fixed to the frame 61 and a plurality of support rollers 66b rotatably attached to the shaft 66a. The plurality of support rollers 66b are disposed at positions respectively corresponding to the plurality of leaves 70 constituting the leaf group 70G. The support rollers 66b are rotatable in a direction in which the upper edge portion 70a and the lower edge portion 70b of the leaf 70 extend. In this embodiment, the leaf 70 is supported by the plurality of support rollers 66b. However, the invention is not limited to this configuration. For example, grooves that guide the leaves 70 in a sliding (movement) direction may be formed at positions corresponding to the leaves 70, respectively, and the leaves 70 may be slid.

That is, each leaf 70 is supported by the frame 61 via the slide support members 66 so as to be individually movable forward and backward in the width direction W.

The frame 61 is provided with a stopper 68 that restricts a movement amount of each leaf 70 toward the rear edge portion 70d side in the width direction W.

As shown in FIG. 4, the motor 91 of the driving device 90 is supported by the base plate 65 provided along each of the side surface portions 61c, 61d of the frame 61.

A rotary encoder 92 that measures a rotation amount of the shaft 95 is disposed inside the driving device 90. The rotary encoder 92 measures the rotation amount of the shaft 95 and outputs the measurement result to the control device 12.

In this way, in the pair of two leaf groups 70G, by advancing and retreating the end surfaces 70c of the leaves 70 constituting the leaf groups 70G in the width direction W to positions corresponding to a desired irradiation field contour shape, an opening having a desired irradiation field shape can be formed between the leaves 70 of the leaf groups 70G facing each other.

Therefore, when the radiation S2 is made incident from the opening 63 in the upper surface portion 61a of the frame 61, a part of the radiation is shielded by the leaves 70 of the leaf groups 70G on both sides, and the patient B is irradiated with the radiation that has passed through the opening formed by the leaf groups 70G.

That is, the therapeutic radiation Sr limited to a predetermined irradiation field shape is generated by the multi-leaf collimator 60.

Although not shown in FIGS. 6 and 7, each leaf 70 has groove-shaped unevenness whose longitudinal direction is the width W direction on both surfaces. The groove-shaped unevenness is formed such that a recess and a protrusion of the adjacent leaves 70 are engaged with each other. This prevents the radiation from reaching the patient B through gaps between the leaves 70 without interfering with the movement of the leaves in the width W direction.

<Configuration of Marker of Multi-Leaf Collimator 60>

Hereinafter, a configuration of a marker 101 fixed to the leaf 70 of the multi-leaf collimator 60 will be described with reference to FIGS. 6 and 7.

As described above, the multi-leaf collimator 60 has a configuration in which two leaf groups 70G, in each of which the plurality of thin plate-shaped leaves 70 made of a material that does not allow radiation to pass therethrough are arranged in the thickness direction, are arranged such that the end surfaces 70c face each other. Main planes of the leaves 70 are arranged so as to be substantially parallel to the radiation irradiation axis Sc.

The marker 101 containing a phosphor is disposed on an end surface (hereinafter referred to as an upper end surface) 70a of the leaf 70 on a radiation source 50 side. Light sources 102a, 102b that irradiate the marker 101 with light for exciting the phosphor, and a camera 103 that captures an image of fluorescence emitted from the marker are disposed at positions where the light sources 102a, 102b and the camera 103 face the upper end surface 70a. An optical system such as a mirror 104 and a condenser lens 105 is disposed between the camera 103 and the marker 101 as necessary.

In the present embodiment, a plate containing a phosphor is used as the marker 101. For example, a plate 101 made of a transparent resin containing a phosphor is used.

As shown in FIGS. 6 and 7, the plate 101 is disposed such that an upper end surface 101a of the plate 101 is located on the upper end surface 70a of the leaf 70.

One surface of the plate 101 is fixed to one surface of the leaf 70 by adhesion or the like.

As the phosphor (fluorescent pigment), any phosphor may be used as long as the phosphor is excited by visible light or ultraviolet light and emits fluorescence having a wavelength whose image can captured by the camera 103.

The upper end surface 101a of the plate 101 may be located on the same plane as the upper end surface 70a of the leaf 70 as shown in (a) of FIG. 8, may protrude from the upper end surface 70a of the leaf 70 by a predetermined amount as shown in (a) of FIG. 9, or may be located at a position where the upper end surface 101a is recessed from the upper end surface 70a of the leaf 70 by a predetermined amount as shown in (a) of FIG. 10.

However, a protrusion amount and a recess amount are set in a range in which an image of the upper end surface 101a of the plate 101 can be captured by the camera 103 ((b) of FIG. 8, (b) of FIG. 9, and (b) of FIG. 10).

At this time, it is desirable that a recess 110 having a depth (thickness direction T of the leaf) equal to or larger than a thickness of the plate 101 (thickness direction T of the leaf 70) is formed in a surface of the leaf 70 to which the plate 101 is fixed, and the plate 101 is fixed in the recess 110. By providing the recess 110, even if the thickness of the plate 101 is ensured to some extent, the plate 101 does not come into contact with the leaf 70 adjacent to the fixed leaf 70, and thus the plate 101 does not interfere with the movement of the leaves 70 while ensuring an amount of the phosphor contained in the plate 101.

It is desirable that the thickness of the plate 101 is approximately half the thickness of the leaf 70 such that the plates 101 of adjacent leaves can be distinguished by image processing.

A length of the plate 101 in the width direction W of the leaf 70 is set to a length required when the upper end surface 101a is recognized as a marker by camera image processing.

A height of the plate 101 (direction of the radiation irradiation axis) is set to a height at which the amount of the phosphor that emits a sufficient amount of fluorescence for the image processing can be ensured, and to a height at which an area capable of obtaining a sufficient adhesive force can be ensured when the plate 101 is bonded to the leaf 70.

In such a configuration, light emitted from the light sources 102a, 102b is applied to the upper end surface 101a of the plate 101. Since the plate 101 is made of a transparent material containing a phosphor, the light emitted from the light sources 102a, 102b reaches the phosphor inside the plate 101 to excite the phosphor. Accordingly, fluorescence is generated not only from the upper end surface 101a of the plate 101 but also from the phosphor inside the plate 101. The fluorescence generated inside the plate 101 propagates through the plate 101, reaches the upper end surface 101a, and is emitted upward from the upper end surface 101a.

The fluorescence emitted from the upper end surface 101 of the plate 101 is reflected by the mirror 104 as shown in FIG. 11, is condensed by the condenser lens 105, and reaches the camera 103, whereby an image thereof is captured.

The control device 12 executes image processing on the image captured by the camera 103, extracts the image of the upper end surface 101a, and detects, for example, a center of the length and width of the image of the upper end surface 101a as a position of the marker (plate 101). The control unit 12 determines whether the detected position of the marker 101 corresponds to a rotation amount of the shaft 95 detected by the encoder 92 of the driving device 90. In a case of correspondence, the control unit 12 continues an operation of radiotherapy as it is. In a case of no correspondence, the control unit 12 determines that an error occurs in which a position of the leaf 70 does not correspond to an intended position, and stops radiation irradiation from the radiation source 50.

In this embodiment, a center position of the marker is detected. However, detection is not limited to the center position. For example, a position of the marker may be detected by recognizing a center of a short side of a rectangle recognized by four corners of the marker or detected length and width.

Alternatively, the control unit 12 may perform feedback control on the driving device 90 based on the detected position of the marker 101.

In this way, in the present embodiment, the upper end surface 101*a* of the plate 101 can be used as a marker by fixing the plate 101, made of the transparent material containing the phosphor, to the surface of the leaf 70 with an adhesive or the like. Accordingly, an adhesion area between the plate 101 and the leaf can be increased, the marker is less likely to peel off, durability is high, a position of the marker can be accurately detected by capturing an image of the marker with the camera, and a position of the leaf can be accurately controlled.

Since the height of the plate 101 (size in the direction of the radiation irradiation axis) can be increased, the amount of the phosphor contained in the plate 101 can be contained to be a necessary amount. The fluorescence emitted inside the plate can propagate, and be emitted from the upper end surface 101*a*. Therefore, since a marker having a large amount of light can be configured, accuracy of marker recognition by image processing can be improved.

It is desirable that the surfaces of the leaves 70 to which the plates 101 are fixed are surfaces on a side that is shadowed from the camera 103 as shown in (*a*-1) of FIG. 12. For example, when an optical axis 103*a* of the camera 103 is located at a center of the leaf group 70G in which the plurality of leaves 70 are arranged in the thickness direction as shown in (*a*-1) of FIG. 12, it is desirable that each plate 101 is fixed to a surface on a side far from the optical axis 103*a* among both surfaces of a respective one of the leaves 70. That is, as shown in (*a*-1) of FIG. 12, surfaces of the leaves 70 in the leaf group 70G, to which the plates 101 are fixed, are bilaterally symmetrical with respect to the optical axis 103*a* in the thickness direction W of the leaves 70.

Accordingly, when the upper end surfaces 101*a* of the plates 101 do not protrude from the upper end surfaces 70*a* of the leaves 70, surfaces 101*b* parallel to main planes of the plate 101 are not unintentionally captured by the camera 103. Therefore, a width of only the upper end surfaces 101*a* recognized as the markers in image processing can be extracted, and the image processing can be performed with high accuracy.

Even when the upper end surfaces 101*a* of the plates 101 protrude from the upper end surfaces 70*a* of the leaves 70 by a predetermined amount, in a case where the plates 101 are fixed to the surfaces on the side far from the optical axis 103*a* as shown in (*a*-1) of FIG. 12, the surfaces 101*b* parallel to the main planes of the plates 101 as shown in (*a*-2) of FIG. 12 have only small protruding portions unintentionally captured by the camera 103, and an influence on the width of the upper end surfaces 101*a* recognized as the markers in the image processing is small.

In contrast, when the plates 101 are fixed to surfaces on the same side of all the leaves 70 in the leaf group 70G as shown in (*b*-1) of FIG. 12, an area of the surfaces 101*b* parallel to the main planes of the plates 101 unintentionally captured by the camera 103 as shown in (*b*-2) of FIG. 12 is larger than that in (*a*-2) of FIG. 12. Therefore, not only an image of the upper end surfaces 101*a* of the plates 101 but also an image of the surfaces 101*b* are recognized as the markers by the image processing, so that accuracy of the markers in a width direction is lower than that in a case of (*a*-2) of FIG. 12.

When the plates 101 are fixed to surfaces on the same side of all the leaves 70 in the leaf group 70G as shown in (*b*-1) of FIG. 12, in a case where positions of adjacent leaves 70 are largely shifted as shown in FIG. 13, an image of the entire surface 101*b* parallel to the main plane of the plate 101 is captured by the camera 103. In this case, since a width of a marker recognized by the image processing includes the entire surface 101*b*, accuracy of the marker in the width direction is lower than that in the case of (*a*-2) of FIG. 12. Therefore, it is desirable that the surfaces of the leaves 70 to which the plates 101 are fixed are the surfaces on the side that is shadowed from the camera 103 as shown in (*a*-1) of FIG. 12.

Even when the surfaces of the leaves 70 to which the plates 101 are fixed are the surfaces on the side that is shadowed from the camera 103 as shown in (*a*-1) of FIG. 12 (that is, when the plates 101 are fixed to the surfaces on the side far from the optical axis 103*a*), in a case where the positions of the leaves 70 are largely shifted and the plates 101 fixed to the leave 70 include, in a mixed manner, ones in which the surfaces 101*b* parallel to the main planes of the plates 101 are exposed to the outside and ones in which the surfaces 101*b* are not exposed to the outside as shown in (*a*) of FIG. 14, an amount of light incident on the plates 101 in which the surfaces 101*b* parallel to the main planes of the plates 101 are exposed is increased, so that an amount of excitation light is larger than that from the other plates 101 of the leaves 70 in which the surfaces 101*b* parallel to the main planes of the plates 101 are not exposed. That is, the surfaces 101*b* parallel to the main planes of the plates 101 are exposed to the outside whatever positions the leaves 70 are located.

Therefore, in these plates 101, the amount of excitation light emitted from the plates 101 is larger than that of the other plates 101, and a bright marker image is obtained, which may result in reduction in accuracy of binarization processing or the like when processing an image captured by the camera 103. Therefore, it is desirable that at least a part of the surfaces 101*b* of the plates 101 are covered with light shielding members 140 as shown in (*b*) of FIG. 14. However, even if a difference in the amount of the light is generated without covering with the light shielding members, an influence on the reduction in the accuracy of the binarization processing is very small as compared with a case where the side surfaces 101*b* described above are visible.

A material that can shield excitation light and external light and is less likely to peel off from the plate 101 is selected as the light shielding member 140. For example, the light shielding member (metal film) 140 that can be formed on a surface of the plate 101 by plating, coating, or the like can be used.

When the upper end surface 101*a* of the plate 101 is disposed so as to protrude from the predetermined upper end surface 70*a* of the leaf 70 by the predetermined amount as in FIG. 9 described above, a side surface 101*c* of a portion of the plate 101 protruding from the leaf 70 as in (*a*) and (*b*-1) of FIG. 15 unintentionally appears an image captured by the camera 103 ((*c*) of FIG. 15). In order to solve this problem, an angle of the side surface may be inclined such that the side surface 101c is shaded by the upper end surface 101a from the camera 103.

For example, as shown in (a) to (c) of FIG. 9 and (b-2) of FIG. 15, each of both side surfaces 101c, in a movement direction W of the leaf 70, of the plate 101 protruding from the predetermined upper end surface 70a of the leaf 70 by the predetermined amount, is inclined so as to form an acute angle with respect to the upper end surface 101a. Accordingly, as shown in FIG. 11, even when the leaf 70 moves, the side surface 101c of the protruding portion of the plate 101 is shaded by the upper end surface 101a and is not unintentionally captured by the camera 103. Therefore, since only the upper end surface 101a is recognized as a marker in the movement direction W by the image processing, recognition accuracy of the marker in the movement direction W can be improved.

Similarly, when the upper end surface 101a of the plate 101 is disposed so as to be recessed from the predetermined upper end surface 70a of the leaf 70 by the predetermined amount as shown in FIG. 10 described above, if the leaf 70 moves in the movement direction W, a positional relationship is formed in which the camera 103 views the upper end surface 101a of the plate recessed in the recess 110 from obliquely above the upper end surface 101a of the plate 101. At this time, an edge portion of the recess 110 in the movement direction W direction partially blocks an angle at which the camera 103 views the entire upper end surface 101a of the plate 101, and the camera 103 cannot capture an image of the entire recessed upper end surface 101a of the plate 101. Therefore, in the present embodiment, upper portions of side surfaces 110a of the recess 110 in the movement direction W is inclined to an angle equal to or larger than a visual angle of the camera 103 so as not to block the visual angle from the camera 103 to entire upper end surface 101a of the plate 101 even when the leaf 70 moves to the maximum movement amount. That is, the side surface 110a is inclined such that a diameter of an opening of the recess 110 in the movement direction W is larger than that of a lower portion of the recess 110. Accordingly, even when the leaf 70 moves, both side surfaces 110a of the recess 110 in the movement direction W does not unintentionally appear in an image captured by the camera 103, and the camera 103 can always capture the image of the entire upper end surface 101a of the plate 101.

For example, as shown in (c) of FIG. 10, each of both side surfaces 110a, in the movement direction W of the leaf 70, formed by the plate 101 being recessed from the predetermined upper end surface 70a of the leaf 70 by the predetermined amount, is inclined so as to form an obtuse angle with respect to the upper end surface 70a. Accordingly, similarly to a case of the plate 101 protruding from the predetermined upper end surface 70a of the leaf 70 by the predetermined amount shown in FIG. 11, even when the leaf 70 moves, both side surfaces 110a in the movement direction W of the leaf 70 are not shaded by the upper end surface 101a of the plate 101 and are not unintentionally captured by the camera 103. Therefore, since only the upper end surface 101a is recognized in the movement direction W by the image processing, recognition accuracy of the marker in the movement direction W can be improved.

REFERENCE SIGNS LIST

10 radiotherapy system
11 therapy planning device
12 control device
20 radiotherapy device
21 ring frame
21a lower end portion
22 moving gantry
22a inner circumferential surface
23 sensor array
24 radiation irradiation device
25 rotation shaft
26A, 26B ray source
27A, 27B sensor array
28 couch
28a upper surface
29 couch driving device
50 radiation source
51 electron beam accelerator
52 X-ray target
53 primary collimator
53h through hole
54 flattening filter
54a protrusion
55 secondary collimator
55h through hole
60 multi-leaf collimator
61 frame
61a upper surface portion
61b lower surface portion
61c, 61d side surface portion
62 leaf accommodating portion
63 opening
64 opening
65 base plate
66 slide support member
66a shaft
66b support roller
68 stopper
70 leaf
70G leaf group
70a upper edge portion
70b lower edge portion
70c front edge portion
70d rear edge portion
70f surface
70g surface
71, 72 slit
71a, 72a upper side portion
71b lower side portion
73 rack gear
90 driving device
91 motor
91a housing
92 rotary encoder
95 shaft
96 pinion gear
101 plate
101a end surface (upper end surface)
101b surface (surface parallel to main plane)
101c side surface (side surface in movement direction W)
110 recess
B patient
C0 isocenter
C1 central axis
C2 central axis
S0 electron beam
S1 radiation
S2 radiation
Sr therapeutic radiation
T plate thickness direction
W width (movement) direction

The invention claimed is:

1. A radiotherapy device comprising:
a radiation source; and
a multi-leaf collimator configured to limit an irradiation range of radiation radiated from the radiation source, wherein the multi-leaf collimator includes:
   a plurality of thin plate-shaped leaves made of a material that does not allow the radiation to pass therethrough, the plurality of thin plate-shaped leaves being arranged in a thickness direction;
   markers, which are plates containing a phosphor, the markers being disposed on predetermined end surfaces of the leaves;
   a light source configured to irradiate the markers with light that excites the phosphor; and
   a camera configured to capture an image of fluorescence emitted from the markers, the camera being disposed at a position where the camera faces the predetermined end surfaces of the leaves, and
wherein, surfaces of the plates are fixed to surfaces of the leaves such that end surfaces of the plates are located on the predetermined end surfaces of the leaves, and an image of the end surfaces of the plates is captured by the camera.

2. The radiotherapy device according to claim 1, wherein the end surfaces of the plates protrude from the predetermined end surfaces of the leaves by a predetermined amount.

3. The radiotherapy device according to claim 1, wherein the end surfaces of the plates are located at positions where the end surfaces of the plates are recessed from the predetermined end surfaces of the leaves by a predetermined amount.

4. The radiotherapy device according to claim 1, wherein recesses having a depth equal to or larger than a thickness of the plates are formed in the surfaces of the leaves to which the plates are fixed, and the plates are fixed in the recesses.

5. The radiotherapy device according to claim 1, wherein the surfaces of the leaves to which the plates are fixed are surfaces on a side that is shadowed from the camera.

6. The radiotherapy device according to claim 1, wherein at least a part of surfaces of the plates fixed to the leaves are covered with a light shielding member on a side not fixed to the leaves.

7. The radiotherapy device according to claim 1, further comprising:
a driving unit configured to move each of the plurality of leaves toward and away from an optical axis of the radiation, wherein
the predetermined end surfaces of the leaves to which the plates are fixed are end surfaces parallel to a movement direction of the leaves.

8. The radiotherapy device according to claim 7, wherein the end surfaces of the plates are disposed so as to protrude from the predetermined end surfaces of the leaves by a predetermined amount, and side surfaces of portions of the plates protruding from the leaves are inclined so as to be shadowed from the camera.

9. The radiotherapy device according to claim 8, wherein the inclined side surfaces of the plates are both side surfaces of the plates in the movement direction.

10. The radiotherapy device according to claim 7, wherein recesses in which the plates are disposed are formed in the predetermined end surfaces of the leaves,
the plates are disposed in the recesses such that upper end surfaces of the plates are located at positions where the upper end surfaces of the plates are recessed from the predetermined end surfaces of the leaves by a predetermined amount, and
portions of side surfaces of the recesses of the leaves, above the upper end surfaces of the plates, are inclined to an angle equal to or larger than an angle at which the camera views the entire upper end surfaces of the plates after movement by the driving unit.

11. The radiotherapy device according to claim 10, wherein
the inclined side surfaces of the recesses are both side surfaces of the recesses of the leaves in the movement direction.

12. The radiotherapy device according to claim 1, wherein the plates are made of a transparent material containing the phosphor, the light emitted from the light source reaches not only the end surfaces of the plates but also the phosphor inside the plates, and the fluorescence emitted inside the plates propagates through the plates, reaches the end surfaces, and is emitted from the end surfaces.

13. A multi-leaf collimator configured to limit an irradiation range of radiation radiated from a radiation source, the multi-leaf collimator comprising:
a plurality of thin plate-shaped leaves made of a material that does not allow the radiation to pass therethrough, the plurality of thin plate-shaped leaves being arranged in a thickness direction;
markers containing a phosphor, the markers being disposed on predetermined end surfaces of the leaves;
a light source configured to irradiate the markers with light that excites the phosphor; and
a camera configured to capture an image of fluorescence emitted from the markers, the camera being disposed at a position where the camera faces the predetermined end surfaces of the leaves,
wherein the markers are plates containing the phosphor, surfaces of the plates are fixed to surfaces of the leaves such that end surfaces of the plates are located on the predetermined end surfaces of the leaves, and an image of the end surfaces of the plates is captured by the camera.

* * * * *